US00PP23078P2

(12) United States Plant Patent
Dümmen

(10) Patent No.: US PP23,078 P2
(45) Date of Patent: Sep. 25, 2012

(54) ***PELARGONIUM* PLANT NAMED 'DUEIMVOR'**

(50) Latin Name: *Pelargonium peltatum×Pelargonium hortorum*
Varietal Denomination: Dueimvor

(75) Inventor: Tobias Dümmen, Rheinberg (DE)

(73) Assignee: Capital Green Investments Ltd., Grand Cayman (KY)

( * ) Notice: Subject to any disclaimer, the term of this patent is extended or adjusted under 35 U.S.C. 154(b) by 79 days.

(21) Appl. No.: 12/928,561

(22) Filed: Dec. 14, 2010

(51) Int. Cl.
*A01H 5/00* (2006.01)

(52) U.S. Cl. ..... Plt./324

(58) Field of Classification Search ..... Plt./325, Plt./332, 324, 330
See application file for complete search history.

*Primary Examiner* — June Hwu
(74) *Attorney, Agent, or Firm* — C. A. Whealy

(57) ABSTRACT

A new and distinct cultivar of interspecific hybrid Geranium plant named 'Dueimvor', characterized by its compact, upright to outwardly spreading plant habit; vigorous growth habit; freely basal branching habit; freely flowering habit; bright red-colored single-type flowers; and good garden performance.

1 Drawing Sheet

Botanical designation: *Pelargonium peltatum×Pelargonium hortorum.*

Cultivar denomination: 'DUEIMVOR'.

BACKGROUND OF THE INVENTION

The present invention relates to a new and distinct cultivar of interspecific hybrid Geranium plant, botanically known as *Pelargonium peltatum×Pelargonium hortorum* and hereinafter referred to by the name 'Dueimvor'.

The new interspecific hybrid Geranium plant is a product of a planned breeding program conducted by the Inventor in Rheinberg, Germany. The objective of the breeding program is to create new uniform interspecific hybrid Geranium plants with dark green-colored leaves and attractive flowers.

The new interspecific hybrid Geranium plant originated from a cross-pollination made by the Inventor in May, 2006 in Rheinberg, Germany of a proprietary selection of *Pelargonium peltatum* identified as code number G00-1870-001, not patented, as the female, or seed, parent with a proprietary selection of *Pelargonium hortorum* identified as code number Z98-2476-4, not patented, as the male, or pollen, parent. The new interspecific hybrid Geranium plant was discovered and selected by the Inventor as a single flowering plant from within the progeny of the stated cross-pollination in a controlled greenhouse environment in Rheinberg, Germany in May, 2008.

Asexual reproduction of the new interspecific hybrid Geranium plant by vegetative cuttings in a controlled greenhouse environment in Rheinberg, Germany since May, 2008, has shown that the unique features of this new interspecific hybrid Geranium plant are stable and reproduced true to type in successive generations.

SUMMARY OF THE INVENTION

Plants of the new interspecific hybrid Geranium have not been observed under all possible environmental conditions. The phenotype may vary somewhat with variations in environmental conditions such as temperature and light intensity without, however, any variance in genotype.

The following traits have been repeatedly observed and are determined to be the unique characteristics of 'Dueimvor'. These characteristics in combination distinguish 'Dueimvor' as a new and distinct interspecific hybrid Geranium plant:

1. Compact, upright to outwardly spreading plant habit.
2. Vigorous growth habit.
3. Freely basal branching habit.
4. Freely flowering habit.
5. Bright red-colored single-type flowers.
6. Good garden performance.

Plants of the new interspecific hybrid Geranium differ primarily from plants of the female parent selection in plant and growth habit as plants of the new interspecific hybrid Geranium are larger and more vigorous than plants of the female parent selection.

Plants of the new interspecific hybrid Geranium differ primarily from plants of the male parent selection in flower color as plants of the new interspecific hybrid Geranium have lighter red-colored flowers than plants of the male parent selection.

Plants of the new Ivy Geranium can be compared to plants of the interspecific hybrid Geranium 'Schöne von Grenchen', not patented. In side-by-side comparisons conducted in Rheinberg, Germany, plants of the new interspecific hybrid Geranium differed primarily from plants of 'Schöne von Grenchen' in the following characteristics:

1. Plants of the new interspecific hybrid Geranium were more compact than plants of 'Schöe von Grenchen'.
2. Plants of the new interspecific hybrid Geranium were more freely branching and had thicker stems than plants of 'Schöne von Grenchen'.
3. Leaves of plants of the new interspecific hybrid Geranium had a distinct zonation pattern whereas leaves of plants of 'Schöne von Grenchen' did not have a distinct zonation pattern.
4. Flowers of plants of the new interspecific hybrid Geranium were single-types whereas flowers of plants of 'Schöne von Grenchen' were double-types.

BRIEF DESCRIPTION OF THE PHOTOGRAPH

The accompanying colored photograph illustrates the overall appearance of the new interspecific hybrid Geranium plant showing the colors as true as it is reasonably possible to obtain in colored reproductions of this type. Colors in the photograph may differ slightly from the color values cited in the detailed botanical description which accurately describe the colors of the new interspecific hybrid Geranium plant. The photograph comprises a side perspective view of a typical flowering plant of 'Dueimvor' grown in a container.

DETAILED BOTANICAL DESCRIPTION

The aforementioned photograph and following observations and measurements describe plants grown during the summer in 10.5-cm containers in a glass-covered greenhouse in Rheinberg, Germany and under practices and conditions which closely approximate commercial interspecific hybrid Geranium production. During the production of the plants, day and night temperatures averaged 18° C. and light levels averaged 4,500 lux. Plants were pinched one time three weeks after planting and were 13 weeks old when the photograph and the description were taken. In the detailed description, color references are made to The Royal Horticultural Society Colour Chart, 1995 Edition, except where general terms of ordinary dictionary significance are used.

Botanical classification: *Pelargonium peltatum*×*Pelargonium hortorum* 'Dueimvor'.

Parentage:

*Female, or seed, parent*.—Proprietary selection of *Pelargonium peltatum* identified as code number G00-1870-001, not patented.

*Male or pollen parent*.—Proprietary selection of *Pelargonium hortorum* identified as code number Z98-2476-4, not patented.

Propagation:

*Type*.—By vegetative cuttings.

*Time to initiate roots, summer*.—About five days at temperatures of 20° C.

*Time to initiate roots, winter*.—About seven days at temperatures of 20° C.

*Time to produce a rooted young plant, summer*.—About three weeks at temperatures of 20° C.

*Time to produce a rooted young plant, winter*.—About four weeks at temperatures of 20° C.

*Root description*.—Fine, fibrous; white in color.

*Rooting habit*.—Freely branching; dense.

Plant description:

*General appearance*.—Compact, upright to outwardly spreading plant habit; uniformly rounded; densely foliated.

*Growth and branching habit*.—Vigorous growth habit; freely basal branching habit with about three basal branches developing per plant.

*Plant height to top of flower umbels*.—About 25 cm.

*Plant height to top of foliar plane*.—About 22 cm.

*Plant width*.—About 20 cm.

*Lateral branches*.—Length: About 6 cm. Diameter: About 8 mm. Internode length: About 2.2 cm. Texture: Pubescent. Strength: Moderately strong. Color: Close to 144B.

Foliage description:

*Arrangement*.—Alternate; simple.

*Length*.—About 3.9 cm.

*Width*.—About 6.2 cm.

*Shape*.—Reniform.

*Apex*.—Acute.

*Base*.—Peltate.

*Margin*.—Crenate.

*Venation pattern*.—Palmate.

*Texture, upper surface*.—Pubescent.

*Texture, lower surface*.—Smooth, glabrous.

*Color*.—Developing and fully expanded leaves, upper surface: Close to 137A; venation, close to 143C. Developing and fully expanded leaves, lower surface: Close to 138A; venation, close to 144B. Zonation pattern: Distance from margin: About 1.5 cm. Width: About 1.5 cm. Color: Close to 136B.

*Petiole*.—Length: About 4.4 cm. Diameter: About 2.4 mm. Texture, upper and lower surfaces: Smooth, glabrous. Color, upper and lower surfaces: Close to 137C.

Flower description:

*Flower arrangement*.—Single-type rotate flowers arranged in rounded hemispherical umbels arising from apical leaf axils; umbels displayed above the foliar plane on moderately strong peduncles; flowers face mostly upright to outwardly.

*Fragrance*.—None detected.

*Quantity of flowers*.—Freely flowering habit; about 15 flowers and flower buds per umbel; about 90 flowers develop per plant.

*Flowering season*.—Year-round under greenhouse conditions; in outdoor nurseries and gardens in Germany flowering is continuous from spring throughout the summer; plants begin to flower about eight weeks after planting.

*Flower longevity*.—Individual flowers last about five to seven days on the plant; flowers persistent.

*Umbel height*.—About 5.5 cm.

*Umbel diameter*.—About 6.4 cm.

*Flower diameter*.—About 4 cm by 4.5 cm.

*Flower depth* (*height*).—About 2 cm.

*Flower buds*.—Length: About 1.2 cm. Diameter: About 5.6 mm. Shape: Ovoid. Color: Close to 44A.

*Petals*.—Quantity per flower/arrangement: Five, in a single whorl. Length: About 2.8 cm. Width: About 2 cm. Shape: Obovate. Apex: Rounded. Base: Attenuate. Margin: Sinuate. Texture, upper and lower surfaces: Smooth, glabrous. Color: When opening and fully opened, upper surface: Close to 43A to 43B; color becoming closer to 44C with development. When opening and fully opened, lower surface: Close to 43A to 43B; color becoming closer to 44C to 44D with development.

*Sepals*.—Quantity per flower/arrangement: Five, arranged in a single whorl. Length: About 1.2 cm. Width: About 2.25 mm. Shape: Ensiform. Apex: Apiculate. Base: Attenuate. Margin: Entire. Texture, upper and lower surfaces: Smooth, glabrous. Color, upper and lower surfaces: Close to 143B.

*Peduncle* (*umbel stem*).—Length: About 1.15 cm. Diameter: About 4 mm. Strength: Moderately strong. Texture: Smooth, glabrous. Color: Close to 144A.

*Pedicel* (*individual flower stem*).—Length: About 2.4 cm. Diameter: About 1.5 mm. Strength: Moderately strong. Texture: Smooth, glabrous. Color: Close to 180A.

*Reproductive organs*.—Androecium: Stamen quantity per flower: About nine Filament length: About 7 mm. Filament color: Close to 41D. Anther length: About 2 mm. Anther shape: Oval. Anther color: Close to 41B. Pollen amount: Moderate. Pollen color: Close to 28A.

Gynoecium: Pistil quantity per flower: One. Pistil length: About 1 cm. Stigma shape: Parted. Stigma color: Close to 44B. Style length: About 2 mm. Style color: Close to 41D. Ovary color: Close to 144A.

*Seed/fruit*.—Seed and fruit development have not been observed.

Disease/pest resistance: Plants of the new interspecific hybrid Geranium have not been observed to be resistant to pathogens and pests common to interspecific hybrid Geraniums.

Garden performance: Plants of the new interspecific hybrid Geranium have been observed to tolerate rain, wind, and temperatures ranging from about 5° C. to about 40° C. and have demonstrated good garden performance.

It is claimed:

1. A new and distinct interspecific hybrid Geranium plant named 'Dueimvor' as illustrated and described.

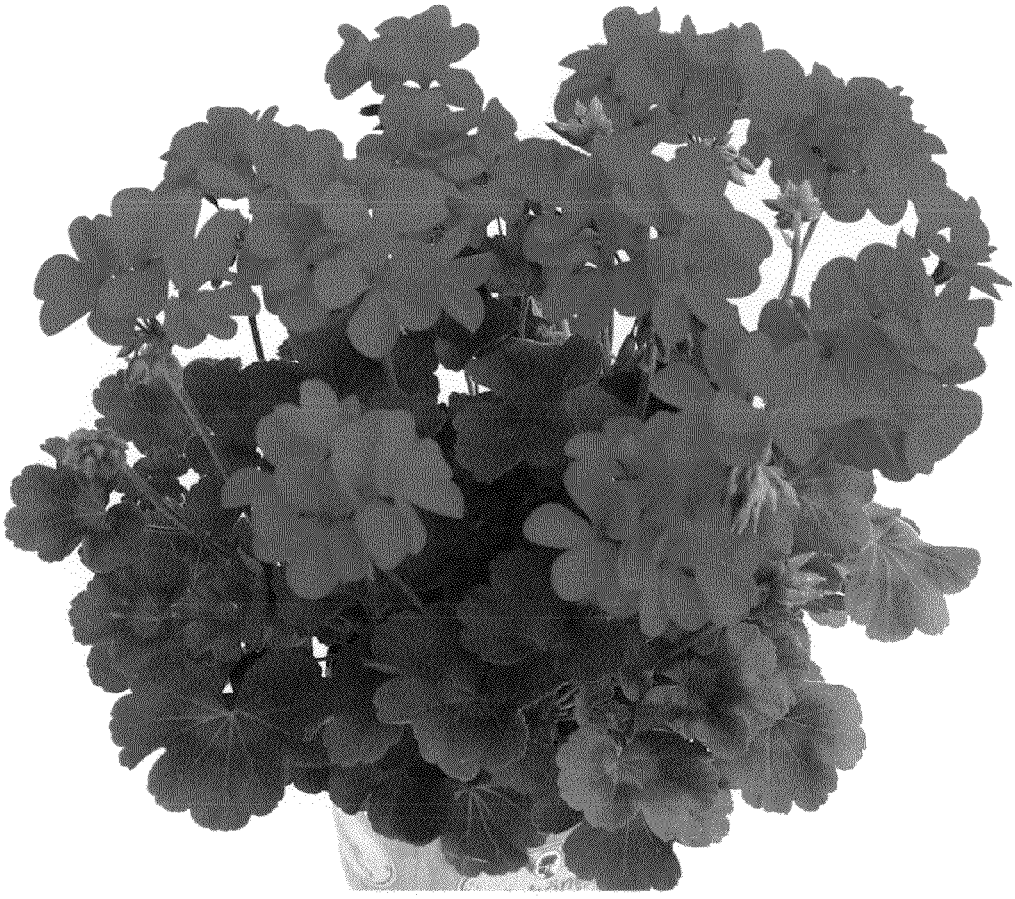

* * * * *